United States Patent [19]

Bhinde et al.

[11] Patent Number: 5,395,988
[45] Date of Patent: Mar. 7, 1995

[54] METAL-LIGAND CATALYZED DECOMPOSITION OF ORGANIC HYDROPEROXIDES

[75] Inventors: Manoj V. Bhinde, Boothwyn; James E. Lyons, Wallingford; Paul E. Ellis, Jr., Downingtown, all of Pa.

[73] Assignee: Sun Company, Inc. (R&M), Philadelphia, Pa.

[21] Appl. No.: 223,090

[22] Filed: Apr. 4, 1994

[51] Int. Cl.6 ............ C07C 29/00; C07C 31/12; C07C 35/14; C07C 33/22
[52] U.S. Cl. .................... 568/835; 568/815; 568/909.8
[58] Field of Search ............ 568/909.8, 835, 815

[56] References Cited

U.S. PATENT DOCUMENTS

| | | | |
|---|---|---|---|
| 4,482,746 | 11/1984 | Hermolin | 568/835 |
| 4,499,305 | 2/1985 | Hermolin | 568/835 |
| 4,910,349 | 3/1990 | Sanderson et al. | 568/909.8 |
| 4,912,266 | 3/1990 | Sanderson et al. | . |
| 4,912,267 | 3/1990 | Sanderson et al. | . |
| 4,922,033 | 5/1990 | Sanderson et al. | 568/909.8 |
| 4,922,034 | 5/1990 | Sanderson et al. | 568/909.8 |
| 4,922,035 | 5/1990 | Sanderson et al. | . |
| 4,922,036 | 5/1990 | Sanderson et al. | . |
| 4,992,602 | 2/1991 | Sanderson et al. | . |
| 5,004,837 | 4/1991 | Baur et al. | 508/835 |
| 5,120,886 | 6/1992 | Lyons et al. | . |
| 5,243,100 | 9/1993 | Sanderson et al. | 568/909.8 |

*Primary Examiner*—Joseph E. Evans
*Attorney, Agent, or Firm*—Q. Todd Dickinson; Stephen T. Falk

[57] ABSTRACT

Organic hydroperoxides are decomposed by drying a reaction mixture containing the organic hydroperoxide and an organic solvent and contacting the dried reaction mixture with a metal organic ligand catalyst under hydroperoxide decomposition conditions. An organic co-solvent for the hydroperoxide may also be used.

31 Claims, No Drawings

METAL-LIGAND CATALYZED DECOMPOSITION OF ORGANIC HYDROPEROXIDES

BACKGROUND

Metallophthalocyanine complexes are known catalysts for the decomposition of hydroperoxides. Sanderson et al U.S. Pat. Nos. 4,912,266 and 4,912,267 issued Mar. 27, 1990; and 4,922,035 and 4,922,036 issued May 1, 1990 disclose decomposition of t-butyl hydroperoxide (TBHP) dissolved in t-butanol (TBA) over a metallophthalocyanine catalyst modified by imidazole and other modifiers. Sanderson et al U.S. Pat. No. 4,992,602 issued Feb. 12, 1991 discloses partial oxidation of isobutane and distillation of the reaction product to obtain a fraction containing 80 to 90% of t-butylhydroperoxide and 20 to 10% of t-butanol, dissolving that fraction in 3 to 10 parts by weight, based on the weight of the fraction, of benzene, and decomposing the hydroperoxide in the resulting solution with a phthalocyanine decomposition catalyst. Lyons and Ellis U.S. Pat. No. 5,120,886 issued Jun. 9, 1992 discloses and claims decomposition of hydroperoxides by contact with metal ligand catalysts of coordination complexes, including phthalocyanine ligands, in which hydrogen in the phthalocyanine molecule has been substituted with electron-withdrawing elements or groups, for example halogen or nitro or cyano groups. Other ligands than phthalocyanines can be used, for example porphyrins and others as subsequently disclosed.

DESCRIPTION OF THE INVENTION

The invention comprises a method for decomposition of organic hydroperoxides to hydroxyl compounds such as alcohols which comprises drying a solution of an organic hydroperoxide in an organic solvent for the hydroperoxide, and contacting the dried solution with a metal organic ligand catalyst as subsequently disclosed. The use of a dried solution of hydroperoxide in solvent results in an increased decomposition rate of the hydroperoxide, compared with the decomposition rate obtained using a hydroperoxide solution which has not been dried. "Drying" means reducing the water content of the hydroperoxide and/or the solvent. Thus, the hydroperoxide may be dried, then dissolved in the solvent, or the solvent may be dried and the hydroperoxide then dissolved in it, or a solution of hydroperoxide in the solvent may be dried, or dried hydroperoxide and dried solvent may be combined. Where a co-solvent is used as described below, the co-solvent may be dried together with or separately from the other components of the reaction mixture, in generally similar fashion.

Drying of Hydroperoxide and/or Solvent

The drying step in the method of the invention may be accomplished by any suitable means for removal of water from organic compounds, such as contact with granular solid drying agents, such as molecular sieves, alumina, silica gel, clays, MgSO$_4$ and the like, azeotropic distillation, contact with organic drying agents such as ethyl orthoformate, preferably regenerable organic drying agents such as diethyl acetals or ketals, for example dimethylacetal, diethylacetal, di t-butyl acetate, 2,2-dialkoxypropanes such as 2,2-dimethoxypropane and the like. Any substantial drying of the hydroperoxide and/or solvent or solvents is within the scope of the invention. Generally, the greater the extent of the drying, up to total or substantially total drying, the greater the beneficial effect on the decomposition rate of the hydroperoxide.

Use of Co-solvent

In one embodiment of the invention, the solvent as previously disclosed, hereinafter sometimes referred to as the primary solvent, is used in conjunction with a co-solvent. Such co-solvent is a solvent different from the primary solvent, which may be added to the hydroperoxide and primary solvent to form a solution of hydroperoxide in the primary solvent and co-solvent. Ketones, such as acetone, methylethylketone, methylisobutylketone and the like, function effectively as co-solvents, resulting in increased rates of decomposition of hydroperoxides, as compared with the use of the primary solvent without a co-solvent, or as compared with the use of either the primary solvent or the co-solvent alone.

Various types of solvents, for example ketones, are capable of functioning either as primary solvents or as co-solvents. When two solvents are used in conjunction, with one solvent present in larger concentration than the other, the one used in the larger concentration is conveniently considered the primary solvent and the other the co-solvent. If they are present in equal amounts, either may be considered the primary solvent. Typically the proportions of primary solvent and co-solvent will be in the range from 1 to 100 parts by volume of co-solvent per 100 parts of primary solvent, but this depends upon the solubility characteristics of a particular pair of solvents in relation to a particular hydroperoxide, and the optimum proportions may be determined by a person skilled in the art in the light of the present specification. The use of more than two solvents is within the scope of the invention.

Hydroperoxides

Hydroperoxides for decomposition according to the invention include compounds having the formula ROOH where R is an organic radical, typically a straight or branched chain alkyl group or cycloalkyl group containing 2 to 15 carbon atoms, an aryl group such as a monocyclic or polycyclic group in which the cyclic groups may optionally be substituted with one or more substituents inert to the decomposition reaction, such as alkyl or alkoxy, containing 1 to 7 carbon atoms, nitro, carboxyl or carboxyl ester containing up to 15 carbon atoms and a halogen atom such as chloride, bromide or an alkylaryl group in which the alkyl chain contains 1 to 15 carbon atoms and the aryl group is as above described. Preferably, R is an alkyl or cycloalkyl group containing 4 to 12 carbon atoms or an alkylaryl group in which the aromatic moiety is phenyl and the alkyl group is straight or branched chain alkyl or cycloalkyl containing up to 6 carbon atoms.

Examples of hydroperoxides for decomposition according to the invention are t-butyl and isobutyl hydroperoxide, isoamyl hydroperoxide, t-amylhydroperoxide, cyclohexyl hydroperoxide, alpha- and beta-ethylbenzene hydroperoxide, cumyl hydroperoxide, phenethyl hydroperoxide and cyclohexylphenyl hydroperoxide; phenethyl hydroperoxide and cumyl hydroperoxide are converted to phenethyl alcohol and cumyl alcohol respectively. Preferred are the alkyl hydroperoxides such as t-butyl hydroperoxide, isoamyl hydroperoxide, and the like, and the cycloalkyl hydroperoxides such as cyclohexyl hydroperoxide, methylcyclohexyl hydroperoxide, and the like.

Hydroperoxide Decomposition Catalysts

Hydroperoxide decomposition catalysts for use according to the invention comprise the transition metal complexes of ligands such as phthalocyanines, porphyrins, porphenes, porphycenes,1,3-bis(arylimino) isoindolines such as "BPI", acetylacetonates, Schiff bases such as salen, saleph and the like, halogenated mono-, bi-, tri- and tetradentate systems such as propanates, buryrates, benzoates, naphthenates, stearates, bipyridines, terpyridines, phenanthrolines, dithiocarbamates, xanthates, salicylaldimines, cyclam, dioxycyclams, pyrazoyl borates and tetraazamacrocycles such as tetramethyltetraazadibenzocycloheptadecane. Preferred are the ligands having the hydrogen atoms of the molecule substantially completely replaced with electron-withdrawing atoms or groups such as halogen, nitro, cyano, halocarbyl, nitrocarbyl, cyanocarbyl and the like.

Preparation of Reaction Mixture

The decomposition catalyst may be slurried in the primary solvent, or if a co-solvent is used, in the co-solvent. The effectiveness of the catalyst may be improved by stirring the catalyst in the solvent or co-solvent for at least 24, and up to 168 or more hours. This time can be reduced by heating the slurry, sonication or other devices known to accelerate both solution and dispersion phenomena. The catalyst slurry may be mixed with a solution of the hydroperoxide in the primary solvent, and the resulting mixture or solution subjected to the reaction temperature as subsequently described.

Solvents and Decomposition Conditions

The decomposition of hydroperoxides according to the invention is typically carried out in a solution of the hydroperoxide in the solvent or solvent mixture. The solution preferably contains from about 5 to about 50 wt % of hydroperoxide. Suitable solvents or co-solvents include benzene, chlorobenzene, o-dichlorobenzene, acetonitrile, benzonitrile, hydroxyl or carbonyl compounds such as alcohols or ketones and the like. A useful solvent is the alcohol formed by decomposition of the hydroperoxide, for example TBA formed by decomposition of TBHP. Any suitable temperature and pressure may be used. Preferably the temperature is in the range from about 25° to about 130° C., and the total pressure from 0 to 500 psig; preferably, the partial pressure of the oxygen in the solution is not more than about 50 psig. The time of reaction may be relatively short, in view of the rapid reaction rate with the catalysts employed according to the invention, and will typically be in the range from about 0.1 to about 5 hours.

The drying of the reaction mixture according to the invention may be effected before contacting the hydroperoxide and solvent or solvents with the decomposition catalyst, or it may be effected in situ in the decomposition reaction.

Drying and Use of Co-solvent

The drying of the reaction mixture according to the invention is applicable to reaction mixtures which contain one solvent, and to reaction mixtures which contain a primary solvent and one or more co-solvents. The use of one or more co-solvents according to the invention is applicable to reaction mixtures which are dried, and to reaction mixtures which are not dried. In a preferred embodiment, the reaction mixture is dried and contains one or more co-solvents.

Integration of Oxidation and Hydroperoxide Decomposition

The hydroperoxide which is decomposed according to the invention may have been obtained from any source. Where the hydroperoxide has been prepared by a noncatalytic or catalytic partial oxidation of hydrocarbons, the decomposition of the hydroperoxide may conveniently be integrated with the previous oxidation. The product mixture from the oxidation typically contains unreacted hydrocarbon, hydroperoxide and alcohol products of the partial oxidation, and water, and is typically fractionated to obtain a fraction comprising a water-containing solution of hydroperoxide in the alcohol product of the oxidation. In the integrated operation, the water-containing oxidation product or a water-containing fraction thereof, is passed to a drying operation wherein the water content is reduced. The product of the drying operation is passed to the decomposition of hydroperoxide according to the invention. Alternatively, the drying operation may be carried out in the decomposition reactor itself, concurrently with the decomposition, rather than in a separate, prior step.

Commercial Production of t-Butanol

In the commercial noncatalytic production of t-butanol ("TBA") by partial oxidation of isobutane, a mixture of TBA and TBHP is typically obtained as reaction product, and the TBHP reacted in a second step with an olefin to produce an alkylene oxide and TBA as products. The invention provides additional options in connection with such operation which may be advantageous in some cases. Thus, for example, the partial oxidation may be conducted either catalytically or noncatalytically to maximize TBHP production relative to TBA production, and the method of the invention used to convert the TBHP produced to TBA in a manner to maximize the overall production of TBA independently of any other product.

Dried Hydroperoxide and Organic Solvent Compositions

The invention also comprises compositions of matter, useful in the methods of the invention, which comprise solutions of an organic hydroperoxide in an organic solvent, prepared by:

(a) drying the hydroperoxide to obtain a dried hydroperoxide and mixing the dried hydroperoxide with the dried or undried solvent, (b) drying the solvent and mixing the dried solvent with the dried or undried hydroperoxide, or (c) drying a mixture of the hydroperoxide and the solvent.

Preferably, the hydroperoxide-solvent or hydroperoxidesolvent-co-solvent composition of the invention contains less than 50%, and more preferably less than 25%, of the water in the corresponding undried composition, that is, the composition consisting of the same relative portions of the same components in their undried state. The compositions also preferably contain less than 1 weight percent, more preferably less than 0.1 weight percent, of water. For example, where the dried composition contains 0.05% water, and the undried composition contains 2% water, the dried composition contains $(0.05/2) \times 100$, or 2.5%, of the water in the undried composition.

EXAMPLES

The following examples illustrate the invention.

Examples 1 through 12

Table I shows the effect of ketonic co-solvent on the decomposition of TBHP, solubilized in t-butyl alcohol ("TBA"), and catalyzed by metal phthalocyanine. TBHP was decomposed in Examples 1 to 12 using metal phthalocyanine as catalyst, and the effect of the addition of ketonic co-solvent was determined by using varying conditions in the twelve runs. The procedure used was as described in footnote a to Table I. The twelve lines of data in Table I are Examples 1 to 12.

("RO$_2$H") had been converted, principally to ROH, where R is t-butyl.

Comparison of Examples 4 through 12 with Examples 1 through 3 shows increased oxygen evolution with at least 38 ppm of catalyst and using ketone as co-solvent, compared with Examples 1 and 2 where no co-solvent was used and Example 3 where acetone was used as co-solvent with only 19 ppm of catalyst.

Examples 13 through 15

Table II shows the effect of added acetone on the decomposition of TBHP using 90, 59 and 59 ppm of Fe[FPc]Cl, the same catalyst as in Examples 1 to 12, at a temperature of 80° C. and pressure of 200 psig, compared with 80° C. and atmospheric pressure in Examples 1 to 12.

TABLE I

DECOMPOSITION OF TBHP CATALYZED BY METAL PHTHALOCYANINE - EFFECT OF KETONIC CO-SOLVENT

| Example | Co-Solvent | Catalyst-ppm$^a$ | Catalyst Stirring Time, Hrs.$^b$ | cc's O$_2$ Evolved in 1st Hr.$^c$ | Time, T$_c$, to Cessation of O$_2$ Evol'n$^d$, hr. | RO$_2$H Conv. % at T$_c$$^e$ | Initial Rate Const., Min.$^{-1}$ |
|---|---|---|---|---|---|---|---|
| 1 | None$^f$ | Fe(FPc)Cl-20 | — | 170 | 8 | 28 | |
| 2 | None$^f$ | Fe(FPc)Cl-80 | — | 630 | 6 | 83 | |
| 3 | Acetone | Fe(FPc)Cl-19 | 2 | 440 | 2 | 30 | 0.034 |
| 4 | Acetone | Fe(FPc)Cl-38 | 24 | 1145 | 2.5 | 82 | 0.11 |
| 5 | Acetone | Fe(FPc)Cl-57 | 2 | 1320 | 1 | 91 | |
| 6 | Acetone | Fe(FPc)Cl-57 | 84 | 1365 | 0.5 | 96 | 0.24 |
| 7 | TBA$^g$ | Fe(FPc)Cl-57 | 84 | 1070 | 4 | 80 | 0.08 |
| 8 | MIBK$^h$ | Fe(FPc)Cl-57 | 24 | 1165 | 1 | 82 | |
| 9 | Acetone | [Fe(FPc)]$_2$O-57 | 144 | 1345 | 0.4 | 95 | |
| 10 | Acetone | Fe(ClPc)Cl-57 | UNK | 820 | 24 | 93 | |
| 11 | Acetone | Fe(ClPc)Cl-114 | 168 | 860 | 22 | 94 | 0.07 |
| 12 | Acetone | Fe(ClPc)Cl-228 | 168 | 1040 | 23 | 98 | 0.09 |

$^a$Unless otherwise noted, the catalyst was slurried for the designated time in the designated co-solvent and a slurry added in 3.9 ml acetone to a solution of 13.8 grams TBHP in 18.1 grams of TBA stirred at 80° C. The amount of catalyst was such as to give a solution containing the ppm level indicated in the Table. The solution was stirred at 78° C. for the designated time. Oxygen evolution was followed manometrically and the liquid product profile monitored by standard glpc.
$^b$Time that the catalyst was stirred in the co-solvent prior to reaction.
$^c$Oxygen evolved (cc's) in the first hour of the reaction.
$^d$Time until all oxygen evolution had ceased.
$^e$[RO$_2$H added - RO$_2$H left)/RO$_2$H added] $\times$ 100
$^f$Solid catalyst added to hot stirred solution (no acetone) in a boat.
$^g$Catalyst slurried in TBA, tert-butyl alcohol, prior to addition.
$^h$MIBK = Methyl Iso Butyl Ketone.

The data under the heading "cc's O$_2$ Evolved in 1st Hr" in Table I indicate the relative effectiveness of the runs. For example, the 1145 cc's of oxygen evolved in the first hour in Example 4 indicates a more effective decomposition than that obtained in Example 3, where the corresponding amount was 440. In Example 6, using acetone as co-solvent and 57 ppm of Fe$^{III}$ perfluoro (F) phthalocyanine (Pc) chloride (Cl) as catalyst, 1365 cc's of oxygen were evolved in the first hour. In Example 6, the catalyst was stirred in the acetone co-solvent for 84 hours prior to contacting the TBHP with the catalyst solution. All oxygen evolution had ceased after 0.5 hour of the reaction, at which time 96% of the TBHP Table II shows the superiority of the method of the invention, in Examples 14 and 15, using acetone as co-solvent, to Example 13, using no co-solvent. Examples 14 and 15 achieved similar results, in terms of % conversion of TBHP, to the results of Example 13, with a smaller catalyst concentration (59 v 90 ppm) and a shorter reaction time 180/195 minutes v 335 minutes).

TABLE II

TBHP DECOMPOSITION
Effect of added Acetone Fe[FPc]Cl catalyst @ 80 C

| EXAMPLE # | RUN # | CAT CONC ppm | % CONV of TBHP | TIME min | PRESSURE psig | TBHP Charge mole % | Acetone Mole % Actual |
|---|---|---|---|---|---|---|---|
| 13 | 3905a | 90 | 78.4 | 335 | 200 | 29.24 | 0 |
| 14 | 3911b | 59 | 72.4 | 195 | 200 | 31.80 | 11.6 |
| 15 | 3925c | 59 | 79.6 | 180 | 200 | 31.68 | 11.6 | a Catalyst (slurried in TBA) heated to 80 C; TBHP added from reservoir, no acetone.
b Catalyst (slurried in TBA) + 1.2 g acetone heated to 80 C; TBHP added from reservoir; 8.7 wt % total acetone.
c Catalyst (slurried in 1.2 g acetone) + TBA heated to 80 C; TBHP added from reservoir; 8.7 wt % total acetone.

Examples 16 through 21

Table III shows the effect of water removal on the decomposition of TBHP catalyzed by metal perhaloporphyrins. In Examples 16, 18 and 20, the t-butyl alcohol ("TBA"), the TBHP and the acetone used were wet, as described in footnote b to Table III. In Examples 17, 19 and 21, the TBA, TBHP and acetone were dry, as also described in footnote b to Table III. In Examples 17, 19 and 21, the cc's of oxygen evolved in the first hour were higher than in the corresponding Examples 16, 18 and 20, indicating that drying the components caused an increase in the effectiveness of the reaction system for decomposition of TBHP. The initial rate constant data confirm the superiority of Examples 17, 19 and 21 using dried components to Examples 16, 18 and 20 using undried components.

was added to a reaction mixture containing no drying agent. And superior conversion of TBHP was obtained in Example 25 where the TBHP was dried prior to addition to the reactor, as compared with Example 24 where the TBHP was added wet to the reaction mixture.

TABLE IV

TBHP DECOMPOSITION
Effect of drying TBHP
Fe[FPc]Cl catalyst @ 80 C

| EXAMPLE # | RUN # | CAT CONC ppm | % CONV of TBHP | TIME min | PRESSURE psig | TBHP Charge mole % | Acetone Mole % Actual |
|---|---|---|---|---|---|---|---|
| 22 | 3917a | 59 | 85.3 | 180 | 0 | 30.80 | 11.6 |
| 23 | 3921b | 59 | 90.7 | 90 | 0 | 31.60 | 11.6 |
| 24 | 3953c | 89 | 95.6 | 60 | 0 | 29.18 | 17.7 |
| 25 | 3955d | 89 | 99.1 | 60 | 0 | 29.18 | 17.7 | a 5.4 g WET TBHP added to the reactor, the reactor contained catalyst (slurried in acetone) and TBA @ 80 C.
b 5.4 g WET TBHP added to the reactor; the reactor contained catalyst (slurried in acetone) and TBA with 2 g activated molecular sieves (3A) @ 80 C.
c 5.4 g WET TBHP, 1.0 g acetone and 7.2 g TBA heated to 80 C in a reactor; catalyst added as acetone slurry in 3 aliquots.
d 5.4 g TBHP (dried using 3A mol sieves), 1.0 g acetone and 7.2 g TBA heated to 80 C in a reactor catalyst added as acetone slurry in 3 aliquots.

Examples 26 through 29

Table V shows the effect of water removal on the decomposition of TBHP catalyzed by metalloporphy-

TABLE III

DECOMPOSITION OF TBHP CATALYZED BY METAL PHTHALOCYANINE - EFFECT OF WATER REMOVAL

| Example | Catalyst-ppm | Dry/Wet[b] | Catalyst Stirring Time, Hrs[c]. | cc's $O_2$ Evolved in 1st Hr.[d] | Time, Tc, to Cessation of $O_2$ Evol'n[e], Hr. | $RO_2H$ Conv. % at $T_c$[f] | Initial Rate Const., Min.$^{-1}$ |
|---|---|---|---|---|---|---|---|
| 16 | Fe(FPc)Cl-57 | Wet | 84 | 1365 | 0.5 | 96 | 0.24 |
| 17 | Fe(FPc)Cl-57 | Dry | 144 | 1440 | 0.1 | 97 | >0.49 |
| 18 | Fe(ClPc)Cl-57 | Wet | 144 | 760 | 4.3 | <87 | 0.05 |
| 19 | Fe(ClPc)Cl-57 | Dry | 168 | 1200 | <17 | 94 | 0.12 |
| 20 | Fe[tBu]$_4$Pc]Cl-19 | Wet | g | 1160 | 3 | NA | 0.17 |
| 21 | Fe[tBu]$_4$Pc]Cl-19 | Dry | g | 1340 | 1 | NA | 0.33 |

[a]Same as footnote a, Table 1.
[b]WET = TBA as purchased from Aldrich (0.05% $H_2O$). TBHP as purchased from Aldrich (90%, 5 wt % $H_2O$), acetone as purchased from Fischer (0.30% $H_2O$). DRY = TBA, TBHP and acetone dried over freshly activated 3A mole sieves before use.
[c]Same as footnote b, Table 1.
[d]Same as footnote c, Table 1.
[e]Same as footnote d, Table 1.
[f]Same as footnote e, Table 1.
[g]Same as footnote f, Table 1.

Examples 22 through 25

Table IV shows the effect of drying TBHP on the subsequent decomposition of the TBHP. In Examples 22 through 24, the TBHP added to the reactor was wet, and in Example 25, the TBHP added to the reactor had been dried as described in footnote d to Table IV. In Example 23, wet TBHP was added to a reactor which contained in the reaction mixture a solid drying agent, activated molecular sieve (3A). Superior conversion of TBHP in a shorter reaction time was obtained in Example 23, where the reaction mixture contained drying agent, as compared with Example 22, where wet TBHP rins. The catalysts used in these examples were metal complexes of porphyrin derivatives: in Examples 26 and 27, $\mu$-oxo dimer of $Fe^{III}$ meso-tetranitro-beta-octaethylporphyrin, and in Examples 28 and 29, $Fe^{III}$ meso-(pentafluorophenyl-betaoctachloroporphyrin) chloride. More cc's of oxygen were evolved in the first hour in Example 26, where the reaction mixture was dry, compared to Example 27, where the reaction mixture was wet. And more cc's of oxygen were evolved in the first hour in Example 28, where the reaction mixture was dry, compared to Example 29 where the reaction mixture was wet.

TABLE V

DECOMPOSITION OF TBHP CATALYZED BY METALLOPORPHYRINS - EFFECT OF WATER REMOVAL

| Example | Catalyst | Dry/Wet[b] | cc's $O_2$ Evolved in 1st Hr[c] | Time, $T_c$, to Cessation of $O_2$ Evol'n[d], hr. | $RO_2H$ Conv. % at $T_c$[e] | Initial Rate Const., Min.$^{-1}$ |
|---|---|---|---|---|---|---|
| 26 | [Fe(TNOEP)]$_2$O | Dry | 1380 | 1.5 | 95 | 0.27 |
| 27 | [Fe(TNOEP)]$_2$O | Wet | 1280 | 2 | 93 | 0.17 |
| 28 | Fe(TPPF$_{20}$Cl$_8$)Cl | Dry | 1350(est.) | >1 | NA | 0.28 |

TABLE V-continued

DECOMPOSITION OF TBHP CATALYZED BY
METALLOPORPHYRINS - EFFECT OF WATER REMOVAL

| Example | Catalyst | Dry/Wet[b] | cc's $O_2$ Evolved in 1st Hr[c] | Time, $T_c$, to Cessation of $O_2$ Evol'n[d], hr. | RO2H Conv. % at $T_c$[e] | Initial Rate Const., Min.$^{-1}$ |
|---------|----------|------------|--------------------------------|-----------------------------------------------|--------------------------|----------------------------------|
| 29 | Fe(TPPF$_{20}$Cl$_8$)Cl | Wet | 1140 | <3 | NA | 0.03 |

$^a$The catalyst, 0.6 mg, was added to a solution of 13.8 grams TBHP in 18.1 grams TBA stirred at 80° C. The solution was stirred at 80° C. for the designated time. Oxygen evolution was followed manometrically and the liquid product profile monitored by standardized glpc.
$^b$Same as footnote b, Table 3.
$^c$Same as footnote c, Table 1.
$^d$Same as footnote d, Table 1.
$^e$Same as footnote c, Table 1.

Examples 30 through 34

Table VI shows the effect of reaction pressure on TBHP decomposition using iron phthalocyanine chloride catalyst at 80° C. The pressure was varied from 0 to 200 psig in five runs. Examples 30 and 31 show the effect of changing the pressure from 0 to 200 psig under wet conditions. The percent conversion of TBHP was higher at 0 psig than at 200 psig. Examples 32 and 33 show the effect of changing the pressure from 0 to 50 psig under dry conditions. The percent conversion of TBHP was higher at 0 psig than at 50 psig.

TABLE VI

TBHP DECOMPOSITION
Effect of reaction pressure
Fe[FPc]Cl catalyst @ 80 C

| EXAMPLE # | RUN # | CAT CONC ppm | % CONV of TBHP | TIME min | PRESSURE psig. | TBHP Charge mole % | TBHP State |
|-----------|-------|--------------|----------------|----------|----------------|---------------------|------------|
| 30 | 3917a | 59 | 85.3 | 180 | 0 | 30.80 | WET |
| 31 | 3925a | 59 | 79.6 | 180 | 200 | 31.68 | WET |
| 32 | 4023b | 65 | 99.0 | 60 | 0 | 27.93 | DRY |
| 33 | 4021c | 83 | 97.4 | 60 | 50 | 26.78 | DRY |
| 34 | 4025d | 101 | 98.6 | 60 | 50 | 25.73 | DRY | a Catalyst (slurried in acetone) + TBA heated to 80° C.; TBHP added from reservoir; N2 sweep @ 10 cc/min
b TBA + TBHP + acetone heated to 80 C in reactor. Catalyst (slurried in acetone added in 3 aliquots.
c TBA + TBHP + acetone heated to 80 C in reactor. Catalyst (slurried in acetone added in 4 aliquots; N2 swwep @ 10 cc/min
d TBA + TBHP + acetone heated to 80 C in reactor. Catalyst (slurried in acetone added in 3 aliquots; N2 swwep @ 10 ccmin

Example 35

Synthesis of Fe(FPc)—O—Fe(FPc)

A quantity of 300 mg of iron perfluorophthalocyanine, Fe(FPc), is stirred in 100 ml of tetrahydrofuran for 12 days in the presence of air. After this time the mixture is filtered through a medium coarse glass fritted funnel and the filtrate evaporated to dryness then heated in vacuo overnight at 110° C. The UV/vis spectrum shows a $\lambda_{max}$ at 628 nm. The mass spectrum shows a signal at M=1728, corresponding to this $\mu$-oxo dimer.

Example 36

Synthesis of Fe[(t-butyl)$_4$Pc]Cl

To a stirring solution of 6.5 g of t-butylphthalic anhydride in 25 ml of 1,2,4-trichlorobenzene is added 7.0 g of urea, 0.2 g of ammonium molybdate and finally 2.55 g of anhydrous FeCl$_3$. The stirred mixture is heated to 190° C. and held there for 4 hr after which time the solution is cooled and filtered. To the filtrate is added 25 ml of petroleum ether (60°–90°). After overnight this material is filtered to give dark blue microcrystalline material. The yield is 35% based on the starting t-butylphthalic anhydride, of Fe[(t-butyl)$_4$Pc]Cl. UV/vis (CHCl$_3$) 608,644 sh. 676 mm.

1.0 g of the Fe[t-butyl)$_4$Pc]Cl is stirred in 20 ml of acetone with 1.0 g of NaN$_3$ for 12 hr. The material is filtered and the filtrate evaporated to dryness. The solids are redissolved in chloroform and washed with H$_2$O then dried over sodium sulfate and evaporated to dryness. The yield is quantitative of Fe[(t-butyl)$_4$Pc]N$_3$ with a $\nu_{N-N}$ in the IR spectrum of 2050 cm$^{-1}$.

The invention claimed is:

1. Method for decomposing organic hydroperoxides which comprises drying a reaction mixture comprising an organic hydroperoxide, an organic solvent for said hydroperoxide, and water, thereby to obtain a dried reaction mixture and contacting said dried reaction mixture with a metal organic ligand catalyst for said decomposing.

2. Method according to claim 1 wherein said hydroperoxide comprises an alkylhydroperoxide.

3. Method according to claim 2 wherein said hydroperoxide comprises t-butyl hydroperoxide.

4. Method according to claim 1 wherein said solvent comprises an alkanol.

5. Method according to claim 4 wherein said solvent comprises t-butanol.

6. Method according to claim 1 wherein said hydroperoxide comprises cyclohexyl hydroperoxide and said solvent comprises cyclohexanol or cyclohexanone or a mixture of cyclohexanol and cyclohexanone.

7. Method of claim 1 wherein said reaction mixture additionally comprises an organic co-solvent for said hydroperoxide.

8. Method according to claim 7 wherein said co-solvent comprises a ketone.

9. Method according to claim 8 wherein said co-solvent comprises acetone.

10. Method according to claim 8 wherein said co-solvent comprises a cyclic ketone containing 6 to 12 carbon atoms.

11. Method according to claim 10 wherein said co-solvent comprises cyclohexanone.

12. Method according to claim 1 wherein said contacting occurs at a temperature in the range from about 25° to about 130° C. and at a total pressure not greater than about 500 psig.

13. Method according to claim 1 wherein said catalyst comprises a metalloperhalophthalocyanine.

14. Method according to claim 1 wherein said catalyst is added incrementally to said reaction mixture.

15. Method of claim 1 wherein said drying of said reaction mixture is in the absence of said catalyst.

16. Method of claim 1 wherein said drying of said reaction mixture is in the presence of said catalyst.

17. Method of claim 16 wherein said hydroperoxide, said solvent, said water and said catalyst are contacted with a granular solid drying agent, thereby to remove water from said reaction mixture and decompose said hydroperoxide.

18. Method of claim 1 wherein said solvent is a hydroxyl-containing organic compound.

19. Method of claim 1 wherein said metal organic ligand catalyst comprises ligand selected from the group consisting of phthalocyanines, porphyrins, porphenes, porphycenes, 1,3-bis(arylimino)isoindolines, acetylacetonates, Schiff bases, and halogenated mono-, bi-, tri- and tetradentate systems.

20. Method of claim 19 wherein said catalyst comprises a metallophthalocyanine.

21. Method of claim 20 wherein said metal comprises iron.

22. Method of claim 20 wherein hydrogen atoms of said phthalocyanine have been replaced with electron-withdrawing atoms or groups.

23. Method of claim 22 wherein said electron-withdrawing atoms or groups are selected from the group consisting of halogen, nitro, cyano, and halocarbyl.

24. Method of claim 23 wherein said catalyst comprises a metallohalophthalocyanine.

25. Method of claim 24 wherein said catalyst comprises a metalloperhalophthalocyanine.

26. Method of claim 19 wherein said catalyst comprises a metalloporphyrin.

27. Method of claim 26 wherein said metal comprised iron.

28. Method of claim 26 wherein hydrogen atoms of said porphyrin have been replaced with electron-withdrawing atoms or groups.

29. Method of claim 28 wherein said electron-withdrawing atoms or groups are selected from the group consisting of halogen, nitro, cyano, and halocarbyl.

30. Method of claim 29 wherein said catalyst comprises a metallohaloporphyrin.

31. Method of claim 30 wherein said catalyst comprises a metalloperhaloporphyrin.

* * * * *